(12) United States Patent
Hossainy et al.

(10) Patent No.: US 8,802,184 B2
(45) Date of Patent: Aug. 12, 2014

(54) MEDICAL DEVICES CONTAINING BIOBENEFICIAL PARTICLES

(75) Inventors: Syed F. A. Hossainy, Hayward, CA (US); Dariush Davalian, San Jose, CA (US); Jinping Wan, Irvine, CA (US); Troy Carter, Manteca, CA (US); Charles Silvis, Salida, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 891 days.

(21) Appl. No.: 11/809,045

(22) Filed: May 30, 2007

(65) Prior Publication Data

US 2010/0100169 A1 Apr. 22, 2010

(51) Int. Cl.
*A61L 33/00* (2006.01)

(52) U.S. Cl.
USPC ......... 427/2.24; 427/2.3; 427/2.25; 427/2.28; 427/230; 427/2.21; 424/423; 424/425; 424/424; 977/906; 623/1.44; 623/1.42; 623/1.47; 623/1.43

(58) Field of Classification Search
CPC .......... A61K 31/56; A61K 9/52; A61K 9/16; A61F 13/00
USPC .......... 424/425, 423, 490, 493, 494, 497, 45, 424/46, 422, 489, 491, 492, 496, 498, 486, 424/427, 429; 623/1.44; 427/2.3, 2.24, 427/2.25, 2.28, 230, 2.21; 604/264, 266
See application file for complete search history.

(56) References Cited

U.S. PATENT DOCUMENTS

| | | | |
|---|---|---|---|
| 4,733,665 A | 3/1988 | Palmaz | |
| 4,800,882 A | 1/1989 | Gianturco | |
| 4,886,062 A | 12/1989 | Wiktor | |
| 5,464,650 A | 11/1995 | Berg et al. | |
| 5,562,922 A * | 10/1996 | Lambert | 424/486 |
| 5,665,382 A | 9/1997 | Grinstaff et al. | |
| 5,837,313 A * | 11/1998 | Ding et al. | 427/2.21 |

(Continued)

FOREIGN PATENT DOCUMENTS

| | | |
|---|---|---|
| WO | WO 00/32238 | 6/2000 |
| WO | WO 01/01890 | 1/2001 |

OTHER PUBLICATIONS

Annemie Rehor "Poly(propylene sulfide) nanoparticles as drug carriers", Thesis, Swiss Fed. Inst. Of Tech., Zurich, Table of Contents and Summary, 4 pgs. (2005).

(Continued)

*Primary Examiner* — Dah-Wei D Yuan
*Assistant Examiner* — Andrew Bowman
(74) *Attorney, Agent, or Firm* — Squire Patton Boggs (US) LLP (57) ABSTRACT

A method of modifying a medical device such as a stent with nano-constructs is disclosed. The method comprises applying a first fluid to the stent; immersing the stent being wet from the first fluid into a second fluid having a suspension of nano-constructs; and removing the stent from the second fluid and allowing the first and second fluid to be removed such that the nano-constructs are carried by the stent for in vivo application of the constructs to a target location of a mammalian subject. The nano-constructs can be attached to the surface of the stent, can be attached to a surface of the coating of the stent, can be embedded into the stent, or can be embedded into the coating.

20 Claims, 4 Drawing Sheets

(56) References Cited

U.S. PATENT DOCUMENTS

| | | |
|---|---|---|
| 5,871,437 A | 2/1999 | Alt |
| 5,886,026 A | 3/1999 | Hunter et al. |
| 6,099,562 A | 8/2000 | Ding et al. |
| 6,117,454 A * | 9/2000 | Kreuter et al. ............... 424/490 |
| 6,143,037 A | 11/2000 | Goldstein et al. |
| 6,287,628 B1 * | 9/2001 | Hossainy et al. ............. 427/2.3 |
| 6,358,556 B1 | 3/2002 | Ding et al. |
| 6,379,379 B1 | 4/2002 | Wang |
| 6,645,517 B2 * | 11/2003 | West et al. ................... 424/422 |
| 6,656,506 B1 | 12/2003 | Wu et al. |
| 6,660,381 B2 | 12/2003 | Halas et al. |
| 6,685,986 B2 | 2/2004 | Oldenburg et al. |
| 6,699,724 B1 | 3/2004 | West et al. |
| 6,702,850 B1 * | 3/2004 | Byun et al. ................... 623/1.44 |
| 6,719,998 B1 | 4/2004 | Golomb et al. |
| 6,746,686 B2 * | 6/2004 | Hughes et al. ............... 424/425 |
| 6,984,404 B1 * | 1/2006 | Talton et al. ................. 424/490 |
| 8,007,855 B2 | 8/2011 | Pacetti et al. |
| 8,017,237 B2 | 9/2011 | Ludwig et al. |
| 8,034,361 B2 | 10/2011 | Hossainy et al. |
| 8,048,441 B2 | 11/2011 | Craig et al. |
| 8,048,448 B2 | 11/2011 | Ludwig et al. |
| 2001/0022988 A1 | 9/2001 | Schwartz et al. |
| 2002/0061363 A1 | 5/2002 | Halas et al. |
| 2002/0132045 A1 | 9/2002 | Halas et al. |
| 2002/0133183 A1 | 9/2002 | Lentz et al. |
| 2002/0187347 A1 | 12/2002 | Halas et al. |
| 2003/0164064 A1 | 9/2003 | Halas et al. |
| 2004/0013792 A1 * | 1/2004 | Epstein et al. ............... 427/2.24 |
| 2004/0052858 A1 | 3/2004 | Wu et al. |
| 2004/0052859 A1 | 3/2004 | Wu et al. |
| 2004/0117007 A1 | 6/2004 | Whitbourne et al. |
| 2005/0056118 A1 | 3/2005 | Xia et al. |
| 2005/0287184 A1 * | 12/2005 | Hossainy et al. ............. 424/423 |
| 2006/0188543 A1 * | 8/2006 | Feng ............................ 424/423 |
| 2007/0055364 A1 | 3/2007 | Hossainy et al. |
| 2007/0148251 A1 | 6/2007 | Hossainy et al. |
| 2007/0259101 A1 | 11/2007 | Hossainy et al. |
| 2007/0292518 A1 | 12/2007 | Ludwig |
| 2008/0051335 A1 | 2/2008 | Kleiner et al. |
| 2009/0148491 A1 | 6/2009 | Hossainy et al. |
| 2010/0222872 A1 | 9/2010 | Kleiner et al. |

OTHER PUBLICATIONS

Hong et al, "Paclitaxel-coated Gianturco-Roubin® II (GR® II) stents reduce neointimal hyperplasia in a porcine coronary in-stent restenosis model", Coron Artery Dis. 12 (6) pp. 513-515 (2001).

Musyanovych et al., "Grafting of Amino Functional Monomer onto Initiator-Modified Polystyrene Particles", Langmuir vol. 21 (6) pp. 2209-2217 (2005).

Prakash et al., "Electrophilic Modification of Polystyrene Nanospheres" J. of Nanoscience and Nanotechnology vol. 5 (3) pp. 397-403 (2005).

Ramos et al., "Modeling the emulsion polymerization of amino-functionalized latex particles", Polymer 47 pp. 1405-1413 (2006).

Ramos et al., "Polymeric and Colloidal Features of Latex Particles with Surface Amino Groups Obtained by Semicontinuous Seeded Cationic Emulsion Polymerization", J. of Polymer Science 43 (17) pp. 3878-3886 (2005).

U.S. Appl. No. 11/804,254, Davalian et al., filed May 16, 2007.

* cited by examiner

Figure 3B

MEDICAL DEVICES CONTAINING BIOBENEFICIAL PARTICLES

FIELD OF THE INVENTION

This invention is generally related to medical devices including implantable medical devices. More particularly, the invention is related to medical devices carrying biobeneficial nano- or microparticles.

DESCRIPTION OF THE STATE OF THE ART

The traditional method of administering therapeutic agents to treat diseases of the internal organs and vasculature has been by systemic delivery. Systemic delivery involves administering a therapeutic agent at a discrete location followed by the agent migrating throughout the patient's body including, of course, to the afflicted organ or area of the vasculature. But to achieve a therapeutic amount of the agent at the afflicted site, an initial dose substantially greater than the therapeutic amount must be administered to account for the dilution the agent undergoes as it travels through the body.

At the other end of the spectrum is local delivery, which comprises administering the therapeutic agent directly to the afflicted site. With localized delivery the initial dose can be at or very close to the therapeutic amount. With time, some of the locally delivered therapeutic agent may diffuse over a wider region, but that is not the intent of localized delivery, and the diffused agent's concentration will ordinarily be sub-therapeutic, i.e., too low to have a therapeutic effect. Nevertheless, localized delivery of therapeutic agents is currently considered a state-of-the-art approach to the treatment of many diseases such as cancer and atherosclerosis.

Localized delivery of therapeutic agents can consist of administering a composition containing a therapeutic agent and a targeting moiety designed to interact specifically with a biochemical entity present at, and exclusive to, the afflicted site in the vasculature. A means to administer the compositions without losing a substantial fraction to the systemic circulation or a means to preferentially localize composition components to an endothelium is, however, lacking in the art.

The present invention provides medical devices for address existing needs for local delivery of therapeutic substances as well as for making implantable medical devices more biobeneficial.

SUMMARY

A method of modifying a medical device such as a stent with nano-constructs is disclosed. The method comprises applying a first fluid to the stent; immersing the stent being wet with the first fluid into a second fluid having a suspension of nano-constructs; and removing the stent from the second fluid for allowing the first and second fluid to be removed such that the nano-constructs are carried by the stent for in vivo application of the constructs to a target location of a mammalian subject. The nano-constructs can be nanoparticles having an average size of less than 650 nm.

In one embodiment, the stent comprises a polymeric component such that the nano-constructs attach to the surface of the polymeric component or become embedded within the polymeric component. The first fluid can be a non-solvent for the polymeric component. The polymeric component can be a coating on the surface of the stent. In some embodiments, the strut structure of the stent is made at least in part from the polymeric component. The polymeric component can be biodegradable.

In some embodiments, the first fluid can be a solvent for the polymeric component, such that the duration of exposure of the first fluid to the polymeric component is limited until a tacky region or a lightly swollen tacky region is formed on the outermost surface of the polymeric component.

In some embodiments the nano-constructs can comprise a polymeric component. The first fluid can be a non-solvent for the polymeric component of the nano-constructs.

The nano-constructs can become embedded into pores or cracks in a surface of the stent or in a surface of a coating deposited on the stent.

The stent and/or nano-constructs can include the same or a different therapeutic agent.

A stent is also disclosed including nano-constructs.

In accordance with another aspect of the invention, a method of treating a vascular disorder is disclosed, comprising implanting the stent having the nano-constructs in the mammalian subject, wherein the disorder can be restenosis or vulnerable plaque.

DETAILED DESCRIPTION

"Constructs" are defined as nano-constructs or micro-constructs and can include a particle form or other than a particle form consisting of a solid mass; a layered formation of materials such as a shell with a core such that the shell or core can include any number of sub-layers; a mixture or blend of materials including physically combined or chemically bonded/conjugated constituents; or any combination of these. The constructs can include metallic, polymeric, or ceramic materials including glass. The constructs can include a bioactive agent. The constructs can include a combination of any of these substances. These materials can form all of the construct or part of the construct. For example, the construct can include a polymeric nanoshell with a bioactive agent core. As another example, the construct can include a metallic nanoshell with a polymeric/bioactive agent blend for the core. The bioactive agent can be coated on the surface of the construct, can be embedded within the construct, can be blended or mixed with a construct material or can be chemically linked or conjugated to the construct.

The construct can be biostable or alternatively biodegradable, bioerodible, biocorrodible, biosoluble, or bioabsorbable. Biodegradable, bioerodible, biocorrodible, biosoluble, or bioabsorbable are terms which are used interchangeably unless specifically indicated. The average size of the construct can be, for example, from 1 nm and about 900 nm, from 1 nm to about 500, from 1 nm to 650 nm, or from 1 nm to about 200 nm. In some embodiments the construct should be less than 250 nm or alternatively less than 650 nm.

Metal can be a pure metal or an alloy. Useful metals include gold or gold alloy. In some embodiments, the metal or metal alloy can include carbon, titanium, silver, platinum, palladium, chromium, iridium, magnesium, zinc, calcium, or tungsten, or alloys thereof. Other materials that can be included in the constructs include dioxide, titanium dioxide, alumina, zirconia, poly(methyl methacrylate) (PMMA), polystyrene, gold sulfide, macromolecules such as dendrimers, semiconductors such as CdSe, CdS, or GaAs. The particles can further have polyvinyl alcohol (PVA), latex, nylon, Teflon, acrylic, Kevlar, or epoxy.

In some embodiments, the construct can be formed of metal colloidal nanoparticles such as colloidal gold nanoparticles. For example, colloidal gold nanoparticles of 3-4 nm size can assemble on nanoparticle surfaces functionalized by amine groups. These nanoparticles act as nucleation sites, and when a gold salt is present in a reducing environment, a solid gold shell can be formed around a nanosize template such as a nanosphere.

In some embodiments, polymeric nanoparticles such as commercially available polystyrene particles modified at their surface to present amine groups may be used as a template for gold nanoshells. Amine functionality can be placed onto these polymers by a variety of techniques. For example, polymeric surface can be modified to have amine functionality via plasma treatment in the presence of ammonia or hydrazine. This plasma process can be carried out by agitation in a plasma reactor. Amino groups can also be incorporated into the end-groups of a polymer (e.g., a biodegradable polymer), if the initiator contains both a hydroxyl group and an amino group protected by a carbobenzoxy group or a t-butoxycarbonyl group, and this initiator is used to make a biodegradable polymer by ring opening polymerization, such as poly(L-lactide) or polyglycolide. After the polymerization, the protecting group can be removed, liberating the amino group. Polymeric methacrylates can be made with amino groups by using a monomer such as N-(3-aminopropyl) methacrylamide. A copolymer with other monomers such has butyl methacrylate or methyl methacrylate can be made. In some embodiments, a dispersion or emulsion polymerization process can be used to form monodisperse nanoparticles with surface amino groups (see, e.g., Ramos; Jose, Forcada; Jacqueline. Polymer 47(4):1405 (2006); Ramos; Jose, Forcada; Jacqueline, Polymer Chemistry 43 (17):3878 (2005); Prakash, G. K. et al., J. of Nanoscience and Nanotechnology 5(3):397 (2005); and Musyanovych, Anna; Adler, Hans-Jurgen Organic Chemistry III Macromolecular Society, 21(6): 2209 (2005).

In some embodiments, the construct can be formed via thiol group facilitated nanoparticle assembling. For example, biodegradable poly(propylene sulfide) can be produced in nanoparticle form as shown by Annemie Rehor (Ph.D. thesis, Swiss Federal Institute of Technology, Zurich, 2005). This polymer has thiol end-groups from the polymerization, which can be maximized in number by exposing the nanoparticles to reducing conditions.

Various other embodiment of polymers that can be used include poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanoate) such as poly(4-hydroxybutyrate), poly(4-hydroxyvalerate), poly(4-hydroxyhexanoate), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly (L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly (tyrosine carbonates) and derivatives thereof, poly(tyrosine ester) and derivatives thereof, poly(imino carbonates), poly (glycolic acid-co-trimethylene carbonate), polyphosphoester, polyphosphoester urethane, poly(amino acids), polycyanoacrylates, poly(trimethylene carbonate), poly (iminocarbonate), polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide-co-lactic acid) (PEO/PLA)), polyalkylene oxides such as poly(ethylene oxide), poly(propylene oxide), poly(ether ester), polyalkylene oxalates, phosphoryl choline, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), biomolecules such as collagen, chitosan, alginate, fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, elastin, or combinations thereof. In some embodiments, the constructs such as the nanoparticles can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly (D,L-lactic acid), poly(L-lactic acid), poly(D,L-lactic acid-co-glycolic acid), or poly(L-lactic acid-co-glycolic acid), respectively.

Upon delivery, the constructs (e.g., nanoparticles) can affect the target site via passive targeting or active targeting. Passive targeting can be achieved by extravasation of the construct through leaky vasculature such as those present in atherosclerotic plaque. In some embodiments, the result of passive targeting can be assessed by the time span after delivery of the nano-constructs and the circulation time of the nano-constructs after delivery. Generally, the longer the constructs remain in circulation, the more the constructs can reach the target site or target tissue, which sometimes is also referred to as the diseased site or diseased tissue. Active targeting can be carried out by attaching a targeting molecule on the constructs (e.g., nanoshells). Targeting molecules include any peptide, antibody, or polysaccharide that has affinity to the target tissue or target site (e.g., atherosclerotic plaque). In some embodiments, the targeting molecule can be a surface-conjugated ligand against a receptor on an inflamed endothelium. Some examples of the targeting molecules are antibodies to CD34, RGD, YIGSR, peptides and antibodies to IIbIIIa, heparin, hyaluronic acid, laminin, collagen, ICAM-1, ICAM-2, ICAM-3, fibrinogen, fibronectin, vitronectin, thrombospondin, osteopontin, integrins, VCAM-1, N-CAM, PECAM-1, IgCAM, folate, oligonucleotide aptamers, selectins, and cadherins.

Attachment of targeting molecule to construct such as to a nanoshell of the construct can be achieved by established methods known to those skilled in the art. The targeting molecule can be attached to the construct via covalent bonding or non-covalent conjugation. Non-covalent conjugation can be based on ionic interaction, hydrogen bonding or other type of interaction. For example, after formation of the gold nanoshell, molecules functionalized with a thiol group can be used to modify the nanoshell surface for targeting of the nanoshell. Thiol-terminated molecules have been shown to self-assemble on gold surfaces. For example, thiol-terminated poly(ethylene glycol) (PEG) having a molecular weight of about 200 Daltons to 10,000 Daltons, preferably between 500 Daltons to about 2,000 Daltons can be used to stealth the nanoshell surface. The other end of the PEG chain can be functionalized with a targeting molecule such as a peptide or an antibody to target the nanoshell to specific tissue within the body.

In some embodiments, the targeting molecule can be attached to the construct via a spacer. A spacer molecule can be a short chain alkyl group such as a C1-C20 alkyl, C3-C20 cycloalkyl, poly(ethylene glycol), or poly(alkylene oxide). Some other spacer molecules can be, but are not limited to, dextran, dextrose, heparin, poly(propylene sulfide), hyaluronic acid, peptides, DNA, PVA and PVP.

The construct described herein can be used to treat, prevent or ameliorate a medical condition. Such a medical condition can be a tumor or nephropathic kidney. In some embodiments, it can be a site of atherosclerosis. Other medical conditions include, but are not limited to, vulnerable plaque, diffuse atherosclerotic disease, diabetic retinopathy, aneurysm, anastomotic hyperplasia, claudication, chronic total occlusion, dysfunctional endothelium, recurring thrombus, fibrin accumulation, or combinations of these.

Preferably, the constructs can be used to treat or to ameliorate a vascular condition such as atherosclerotic plaque, vulnerable plaque, peripheral arterial disease, vascular inflammation, diffuse atherosclerotic disease, or restenosis. As used herein, "treating" refers to the administration of a therapeutically effective amount of a bioactive agent to a patient known or suspected to be suffering from a vascular disease.

As used herein, an "atherosclerotic plaque" refers to a deposit of fatty substances, cholesterol, cellular waste products, calcium and/or fibrin on the inner lining or intima of an artery.

Vulnerable plaque on the other hand is quite different from either atherosclerosis or restenosis. Vulnerable plaque occurs primarily within the wall of a vessel and does not cause prominent protrusions into the lumen of the vessel. It is often not until it is "too late," i.e., until after a vulnerable plaque has broken and released its components into the vessel, that its presence is even known. Numerous methods have and are being investigated for the early diagnosis of vulnerable plaque but to date none have proven completely successful.

The intrinsic histological features that may characterize a vulnerable plaque include increased lipid content, increased macrophage, foam cell and T lymphocyte content, and reduced collagen and smooth muscle cell (SMC) content. This fibroatheroma type of vulnerable plaque is often referred to as "soft," having a large lipid pool of lipoproteins surrounded by a fibrous cap. The fibrous cap contains mostly collagen, whose reduced concentration combined with macrophage derived enzyme degradations can cause the fibrous cap of these lesions to rupture under unpredictable circumstances. When ruptured, the lipid core contents, thought to include tissue factor, contact the arterial bloodstream, causing a blood clot to form that can completely block the artery resulting in an acute coronary syndrome (ACS) event. This type of atherosclerosis is coined "vulnerable" because of the unpredictable tendency of the plaque to rupture. It is thought that hemodynamic and cardiac forces, which yield circumferential stress, shear stress, and flexion stress, may cause disruption of a fibroatheroma type of vulnerable plaque. These forces may rise as the result of simple movements, such as getting out of bed in the morning, in addition to in vivo forces related to blood flow and the beating of the heart. It is thought that plaque vulnerability in fibroatheroma types is determined primarily by factors which include: (1) size and consistency of the lipid core; (2) thickness of the fibrous cap covering the lipid core; and (3) inflammation and repair within the fibrous cap.

An example of disorders that vessel inflammation is involved is vulnerable plaque (VP) rupture. Previous studies have demonstrated that inflammation promotes proliferation at sites of balloon angioplasty and stent placement in pigs (Kornowski, et al., Coron Artery Dis. 12(6):513-5 (2001)). Since sites of vulnerable plaque have a higher density of macrophages and lymphocytes than other types of atherosclerotic lesions, it is expected that these sites, when stented, will produce elevated amounts of the cytokines (IL-1, TNF-alpha) that promote smooth muscle cell proliferation.

Another example of disorders that vessel inflammation is involved is diabetes. Studies have shown that patients with type-2 diabetes have higher rates of restenosis than the general population. The diabetic patient is in pro-inflammatory state that can amplify restenosis because diabetic lesions contain a large number of inflammatory cells (e.g., macrophages, lymphocytes, etc.). Accordingly, the method of the present invention is also particularly useful for diabetic patients.

As used herein, "restenosis" refers to the re-narrowing or blockage of an artery at or near the site where angioplasty or another surgical or interventional procedure was previously performed to remove or treat stenosis or other vascular disorders or constrictions.

As used herein, a "peripheral arterial disease" refers to a condition similar to coronary artery disease and carotid artery disease in which fatty deposits build up in the inner linings of the artery walls thereby restricting blood circulation, mainly in arteries leading to the kidneys, stomach, arms, legs and feet.

A "bioactive agent" as described above to be included with construct refers to any substance that is of medical or therapeutic, diagnostic or prophylactic utility.

A therapeutic bioactive agent further refers to a bioactive agent that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease;

(2) slowing the progress of the disease; (3) causing the disease to regress; or (4) alleviating one or more symptoms of the disease.

A bioactive agent also refers to an agent that, when administered to a patient, either prevents the occurrence of a disease or disorder or retards the recurrence of the disease or disorder. Such a bioactive agent may be referred to as a prophylactic bioactive agent. As used herein, a "patient" refers to any organism that can benefit from the administration of a bioactive agent. In particular, patient refers to a mammal such as a cat, dog, horse, cow, pig, sheep, rabbit, goat or a human being.

Suitable antiproliferative agents include, without limitation, actinomycin D, or derivatives or analogs thereof, i.e., actinomycin D is also known as dactinomycin, actinomycin IV, actinomycin $I_1$, actinomycin $X_1$, and actinomycin $C_1$. Antiproliferative agents can be natural proteineous agents such as a cytotoxin or a synthetic molecule, all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, pirfenidone, prodrugs thereof, co-drugs thereof, and combinations thereof.

Suitable anti-inflammatory agents include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecrolimus, prodrugs thereof, co-drugs thereof, and combinations thereof. The anti-inflammatory agent may also be a biological inhibitor of proinflammatory signaling molecules including antibodies to such biological inflammatory signaling molecules.

Suitable antineoplastics and/or antimitotics include, without limitation, paclitaxel, docetaxel, methotrexate, azathioprine, vincristine, vinblastine, fluorouracil, doxorubicin hydrochloride, and mitomycin.

Suitable antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä (Biogen, Inc., Cambridge, Mass.), calcium channel blockers (such as nifedipine), colchicine, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6, 6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.).

Suitable cytostatic or antiproliferative agents include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide. Suitable antiallergic agents include, without limitation, permirolast potassium.

Other suitable bioactive agents include, without limitation, alpha-interferon, genetically engineered epithelial cells, synthetic inorganic and organic compounds, proteins and peptides, polysaccharides and other sugars, lipids, and DNA and RNA nucleic acid sequences having therapeutic, prophylactic or diagnostic activities, nucleic acid sequences include genes, antisense molecules which bind to complementary DNA to inhibit transcription, and ribozymes. Some other examples of suitable bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy; antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinson's disease drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Preferred bioactive agents include a corticosteroid, everolimus, zotarolimus, sirolimus, a sirolimus derivative, paclitaxel, a bisphosphonate, ApoA1, a mutated ApoA1, ApoA1 milano, an ApoA1 mimetic peptide, an ABC A1 agonist, an anti-inflammatory agent, an anti-proliferative agent, an anti-angiogenic agent, an antifibrotic agent, a profibrotic agent, an antithrombotic agent, a matrix metalloproteinase inhibitor or a tissue inhibitor of metalloproteinase.

The amount of bioactive agent in a bioactive agent formulation will depend on the required minimum effective concentration (MEC) of the agent and the length of time over which it is desired that the MEC be maintained. For most bioactive agents the MEC will be known to, or readily derivable by, those skilled in the art. For experimental bioactive agents or those for which the MEC by localized delivery is not known, the MEC can be empirically determined using techniques well-known to those skilled in the art.

In the embodiments of the present invention, an implantable medical device can be used to carry the constructs. "Carried" is defined as permanently carry until the device is removed from the patient or is fully absorbed in the patient. "Carried" can also mean that the construct is able to release from the device during a period which the device is under use. The period of release can be strategically defined by the manufacturer. For example, a layer of bioabsorbable polymer can be used as a trigger mechanism for the release of the construct to the area in need of treatment.

"Implantable medical device" is defined as a medical device that is intended to be fully or at least partially implanted in a mammalian patient. The implantation can be permanent or temporary. Examples of such medical devices include self-expandable stents, balloon-expandable stents, stent-grafts, grafts (e.g., aortic grafts), heart valve prostheses, cerebrospinal fluid shunts, pacemaker electrodes, catheters, endocardial leads, anastomotic devices and connectors, orthopedic implants such as screws, spinal implants, and hip or knee replacement devices. The underlying structure of the device can be of virtually any design. The device can be made of a metallic material or an alloy such as, but not limited to, cobalt chromium alloy (ELGILOY®), stainless steel (316L), high nitrogen stainless steel, e.g., BIODUR® 108, cobalt chrome alloy L-605, "MP35N," "MP20N," ELASTINITE® (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable (e.g., bioabsorbable stent) or biostable polymers could also be used with the embodiments of the present invention. In some embodiments, the stent can be made from and/or coated with poly(lactic acid-co-glycolic acid) (PLGA), polylactic acid (PLA), polycaprolactone (PCL), or a combination of these polymers.

In some embodiments, the stent such as a metallic stent can be coated with ethylene vinyl alcohol copolymer (EVAL), poly(vinylidene fluoride) (PVDF), poly(vinylidene fluoride-co-hexafluoropropylene) (PVDF-HFP), or any of the aforementioned polymers. The coating can include a bioactive agent such as any of those listed above, including everolimus for example.

In some embodiments, the stent (and/or coating for the stent) and the constructs (e.g., nanoparticles) are made from poly(lactic acid-co-glycolic acid) (PLGA), polylactic acid (PLA), or polycaprolactone (PCL).

Figure 1:
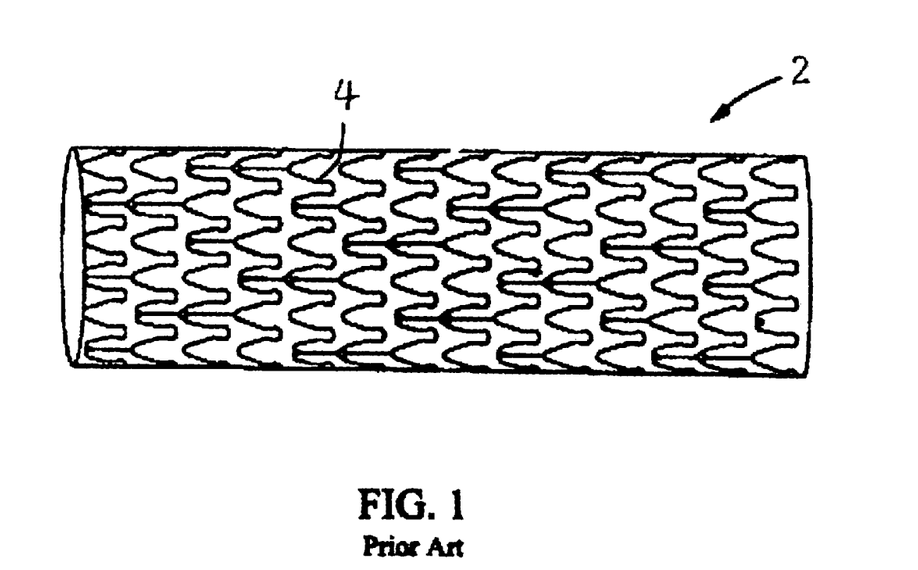
FIG. 1 shows a conventional stent.

Preferably, the implantable medical device is a stent such as a balloon example stent or self-expandable stent. U.S. Pat. No. 4,733,665, issued to Palmaz; U.S. Pat. No. 4,800,882, issued to Gianturco; and U.S. Pat. No. 4,886,062, issued to Wiktor disclose examples of stents. One example of a stent 2 which includes struts 4 is illustrated in FIG. 1. Stents have tubular bodies with a variety of unique strut patterns and strut geometrical configurations, sometimes with spacing or gaps between the struts.

The devices can be bare or without a coating or can include a coating. The coating can include a polymeric material and optionally a bioactive agent mixed, combined or blended with the polymeric material. The agent can be chemically bonded or conjugated to the polymer. Alternatively, the device can include a "neat" layer of a bioactive agent without a polymeric matrix. Any of the aforementioned polymers and bioactive agents can be used as the coating. The bioactive agent of the construct can be the same as or different than the bioactive agent used with the coating. For example, a nanoparticle can include an anti-lipid drug and the coating can include everolimus for the treatment of restenosis. The coating can include multiple layers such that each layer can be the same polymer or a different polymer. Each layer can be made of the same polymer or different polymer. Each layer can be bioactive agent free or can include one or combination of the same or different bioactive agents.

The constructs, e.g., nanoparticles, of the present invention can be disposed on the surface of the device or the coating on the device; embedded within the body of the device or the coating on the device such that they are completely covered or partially covered; and/or can be embedded within depots, cavities, pores or cracks on the surface of the device or on the coating supported by the device. The loading density of the construct or nanoparticles can be from 10 mg/ml to 10,000 mg/ml, preferably 10 mg/ml to 500 mg/ml, for example. The depots, cavities, pores or cracks can be a natural part of the material from which the device is made, can be a product of the manufacturing of the device, or can be intentionally made during or subsequent to manufacturing of the device. Processes used can include bead blasting, chemical etching, laser removal, salt extraction techniques, all of which are well know in the art.

The constructs, e.g., nanoparticles can be physically included with the polymer during the extrusion process of forming the device such as a polymeric stent. The constructs can be blended with a coating composition including a polymer, solvent and optionally an active agent and then sprayed on the device or the device can be immersed in the composition. The constructs can be physically forced into the device or the coating on the device. In one embodiment, a coated stent or a polymeric stent can be rolled over a bed of the nanoparticles to physically force the particles into the stent or into the coating of the stent.

In some embodiments, a composition can be used to embed the construct into the device, embed into the coating of the device, or simply attach the construct onto the surface of the device or the surface of the coating. The device (e.g., metal stent with a polymeric coating or a polymeric stent with or without a polymeric coating) is first prepared by contacting with a first fluid or fluid mixture. In some embodiments, the first fluid can be a non-solvent. Non-solvent is intended to include a non-solvent for the stent, the stent coating or the construct (e.g., nanoparticle). In some embodiments, the fluid can be a solvent for the stent, the stent coating, or the construct (e.g., nanoparticle). Exposure to the solvent should be of a sufficient duration to merely allow for the surface (e.g., outermost region) of the stent, the coating or the construct to become tacky or sticky and/or slightly swollen. The exposure should not damage the stent, remove the coating, or dissolve the nano-particle into the solvent.

A second fluid including a suspension of the construct (e.g., nanoparticle) is prepared such as an aqueous nanoparticle suspension. The first fluid should be selected to enhance retention of the nanoparticle on the substrate and to result in a uniform loading across the length of the substrate. The device having the first fluid thereon (e.g., an at least partially "wet" or completely "wet" device) is then exposed to, such as by dipping, the nanoparticle containing second fluid. In some embodiments, the first fluid can be partially dried off such that any excessive amount can be removed. The exposure should be long enough so as to allow the constructs (e.g., nanoparticles) to be carrier by the device such as carried by the surface of the device or the coating on the device, or embedded within the device or the coating of the device. The constructs or nanoparticles can migrate and be imbedded in the depots, pores, cavities or the cracks. If the first fluid swells the polymer, the polymer should remain at least partially swollen until sufficient amount of the constructs are embedded within the polymer. Thereafter, once the first fluid is removed, the polymer will collapse, entrapping the constructs. After a determined amount of time, the exposure of the device to the construct suspension is terminated. The device can then be washed so as to remove excess or loose constructs or nanoparticles. The washing step can be performed by a non-solvent to any of the polymeric components. A drying step can also be employed to remove the first and second fluid as well as the wash.

Examples of non-solvents and solvents depend on the type of device and nanoparticles used. Examples include ethanol, methanol, freon, heptane, hexane, caprolactone, dimethyl formamide, N-methyl pyrrolidone, cyclohexanone, 1, 1, 2 trichloromethane, ethyl acetate, acetone, acetonitrile, chloroform, dichloromethane, tetrahydrofuran, and methyl isobutyl ketone. A combination or mixture of solvents can also be used.

Examples of fluid carrier for the construct include water, phosphate buffered saline (PBS), cell culture medium such as Dulbecco's Modified Eagle's Medium (DMEM) and albumin solution in phosphate buffered saline (PBS).

In some embodiments, immobilizing agents can be used for attaching or embedding of the constructs (e.g., nanoparticles), including adding an amount (0.1% to 50% w/w) of a solvent, such as those listed above, into the fluid carrier such that upon dipping of the stent into the carrier the constructs immobilize on the surface by sintering based on the added solvent. In other words, the stent is first dipped in the construct suspension followed by adding of the immobilizing agent or the immobilizing agent is first added followed by dipping of the stent. The agent can be acetone, DMAC etc. added into the carrier fluid. Alternatively, but not mutually exclusively, the agent can be an adhesive polymer such as hyaluronic acid, polyhydroxypropyl methacrylamide (PHPMA), polycarboxymethyl cellulose (PCMC), gelatin, silk-elastin, elastin-collagen blend, or polyacrylic acid added in the construct suspension carrier fluid.

In some embodiments, these adhesive polymers or others as listed above can be used as a top-coat layer for retention of the constructs on the stent.

In one embodiment, different sized nanoparticles and micro-particles will be deposited by dipping the stent first into a larger average size particle suspension (e.g., 400-1000 nm) and subsequently dipping into a second suspension of a smaller average size (e.g., 100-300 nm). The different size particle can have the following design feature: (1) the release rate of drug will be tailored by the size (e.g., larger size release slower than smaller size); or (2) the larger size particles by design can be less adherent on the stent surface and hence can release from the stent at faster rate than the smaller size. This will result in a regional treatment in case of diffuse disease. The sequence of dipping can also be reversed.

The design features can also be obtained by having the first population of particle (larger size particle or smaller size particle) selected from a polymer that will have lesser adherence compared to the second population. For example 1-PLA based particle may stick less compared to PEA or polybutylene succinate, or polyglycerol sebacate due to lower Tg and higher propensity to solvent sintering.

EXAMPLE 1

A stent on a catheter and coated with co-poly{[N,N'-sebacoyl-bis-(L-leucine)-1,6-hexylene diester]-[N,N'-sebacoyl-L-lysine 2,2,6,6-tetramethyl-4-amino-1-piperidinyloxyl amide]} (PEA-TEMPO) was dipped into a mixture of hexane:DCM (90:10) for 5 minutes. The stent was then taken out and briefly dried under a chemical hood for 30 seconds. A suspension of 650 nm PLGA nanoparticles (Lactide:Glycolide (L:G) 50:50 ratio) that had been dyed with CY5 dye for visualization under the fluorescence microscope was prepared. The stent was dipped for 10 minutes in the nanoparticle suspension and then was washed thoroughly with deionized water. The stent was then incubated with 4 ml of phosphate buffer (pH =7.4) and 10% porcine serum at 37 deg. C. in an incubator on a shaker for 1 hour to remove any loose or weakly bonded nanoparticles. The stent was then washed with deionized water and dried overnight in a freeze drier. The stent was observed under a fluorescence microscope that indicated attachment of the nanoparticles to the surface.

EXAMPLE 2

A stent coated with PEA-TEMPO was immersed into a mixture of pentane and acetone (95:30) for 30 seconds. The stent was taken out from the solvent mixture and briefly dried for a minute under a chemical hood. The stent was then immersed into a suspension of 650 nm CY5 dyed PGLA nanoparticles (L:G 50:50) for ten minutes. The stent was washed with deionized water and dried overnight in vacuum. The fluorescent microscope indicated uniform attachment of nanoparticles to the surface.

EXAMPLE 3

A stent coated with D, L PLA was immersed into a mixture of pentane and acetone (95:5) for 30 seconds. The stent was taken out from the solvent mixture and briefly dried for one minute under a chemical hood. The stent was then immersed into a suspension of 200 nm CY5 dyed PLGA nanoparticles (L:G 50:50) for ten minutes. The stent was then washed with deionized water and dried overnight in vacuum. The stent was examined by fluorescent microscope that indicated attachment of nanoparticles to the surface.

It is predicted that the nanoparticle loading density and retention will allow migration in the vicinity of the target lesion and regionally treat other non-culprit lesions for prevention and progression of diseases in these secondary lesions.

EXAMPLE 4

Figure 2:
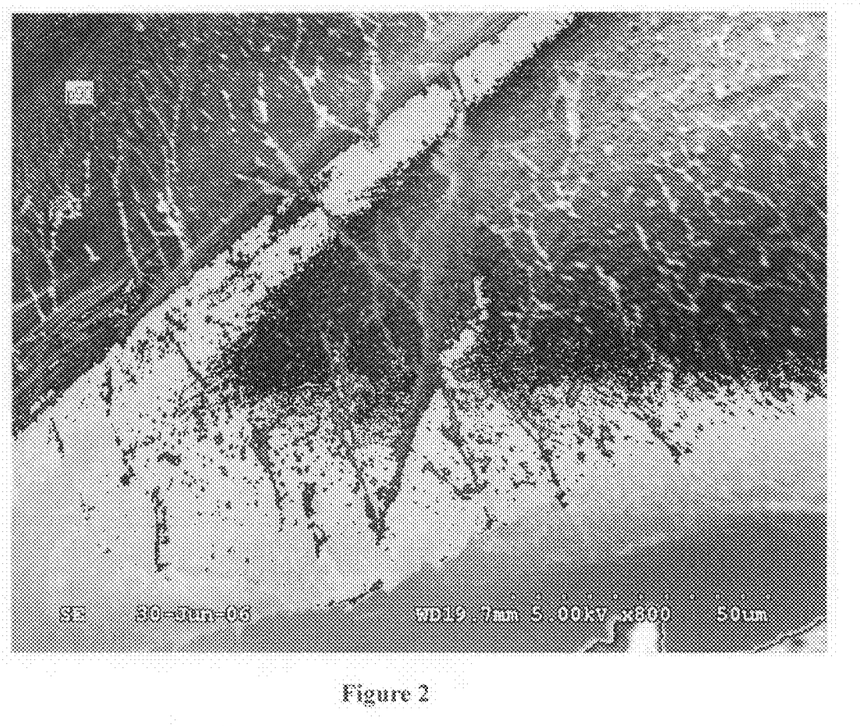
FIG. 2 is a scanning electron microscope (SEM) image of a stent surface in accordance with Example 4.

A PLA polymer stent was dipped into a suspension of 250 nm PGLA nanoparticles (L:G 50:50) that had been dyed with CY5 for visualization under fluorescence light microscope. The stent was dipped for 10 seconds in the nanoparticle suspension and then was washed thoroughly with deionized water. The stent was then incubated with 2 ml of a PBS (pH +7.4) at room temperature on a shaker. At 30 minute and 1 hour interval, 200 ul of the PBS was withdrawn and examined for fluorescent of CY5 in a plate reader. At none of these time points was there any detectable CY5 fluorescent measured. The stent was washed with deionized water and then dried overnight on a freeze drier. The stent was looked at under a fluorescence microscope. There was indication of nanoparticles on the surface of the stent. An SEM image of the surface is provided by FIG. 2.

EXAMPLE 5

A piece of PLA polymeric stent was immersed into a mixture of pentane:dichloromethane (DCM), 80:20 for ten minutes. The stent was then briefly air dried and was dipped into the suspension of 650 nm CY5 dyed nanoparticles for another ten minutes. The stent was then washed with deionized water and added to porcine serum (4 ml). The stent was shaken at 37 deg. C. in an incubator for 30 and 60 minutes. 100 ul of samples were taken at each time point for fluorescent measurements. The stent was then washed with deionized water and dried overnight on a freeze drier.

The above experiment was repeated with a different mixture ratio of pentane:DCM: 85:15, 90:10, 95:5 and pure pentane.

Figure 3A:
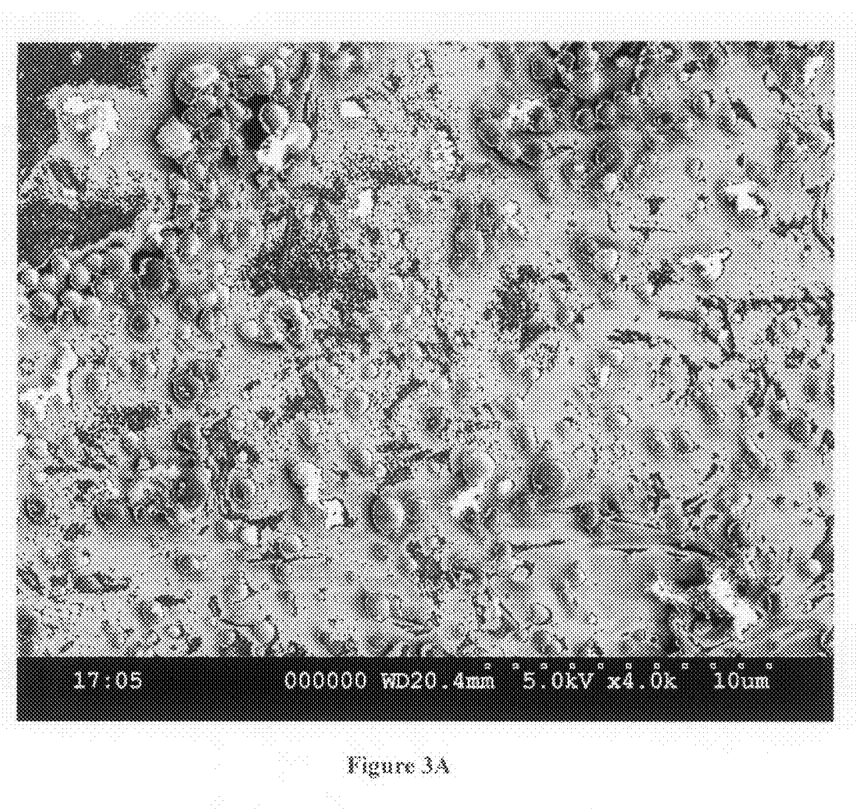
FIGS. 3A and 3B are sample SEM images for Example 5.
Figure 3B:
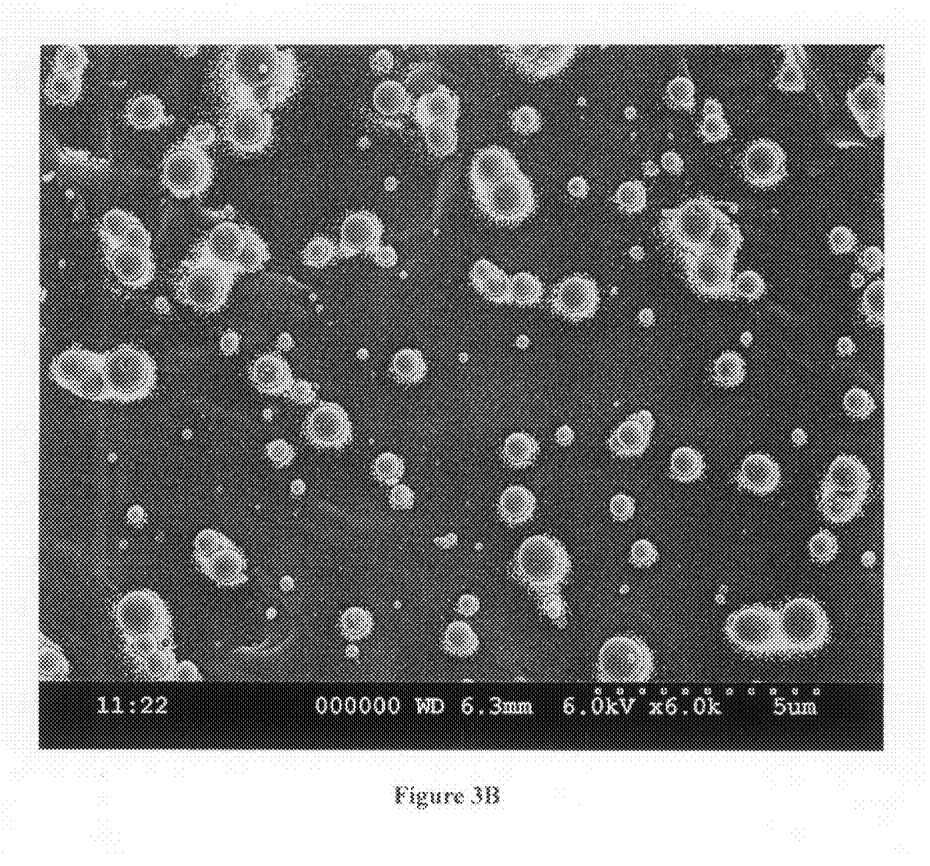

The results from all the above experiments have shown a uniform attachment of the particles to the stent surface. FIGS. 3A and 3B are sample SEM images for this example.

EXAMPLE 6

A D,L lactide polymeric stent was immersed into a mixture of pentane and acetone (95:5) for 30 second. The stent was taken out from the solvent mixture and briefly dried (1 min.) under a chemical hood. The stent was then immersed into a suspension of 650 nm CY5 dyed PLGA nanoparticles (L:G 50:50) for ten minutes. The stent was then washed with deionized water and dried overnight in vacuum.

EXAMPLE 7

A D,L PLA polymeric stent was immersed into a mixture of pentane and acetone (95:5) for 30 second. The stent was taken out from the solvent mixture and briefly dried (1 min.) under a chemical hood. The stent was then immersed into a suspension of 160 nm CY5 dyed PLGA nanoparticles (L:G =50:50) for ten minutes. The stent was then washed with deionized water and dried overnight in vacuum.

It is believed that, with a drug loading, this type of nanoparticle loading density and retention can allow for migration in the vicinity of the target lesion and treat other non-culprit lesion regionally for prevention and progression of diseases in secondary lesions.

EXAMPLE 8

A metal stent having a depot pattern was loaded with nanoparticles into the depots as well as on the non-depot metal surface. Acetone was added in dope amount into an aqueous suspension of polystyrene beads. Acetone was required to sinter the nanoparticles to the stent surface. The formulation consisted of 22.5% polystyrene beads (highly concentrated by centrifuge) and 77.5% acetone. The process steps included: (1) Dipping stent into formulation two times followed by air drying; (2) Fluorescent imaging; (3) Saline dipping at 37 deg. C. for 10 minutes; (4) Vacuum dry ½ hour; and (5) Fluorescent imaging; (6) Saline dipping at 37 deg. C. for 20 minutes; (7) Vacuum dry ½ hour; and (8) Fluorescent imaging. The result was adequate depot filling and no degradation in fluorescents signal after 30 minute saline dips.

EXAMPLE 9

Generally the same as Example 8 but carboxy methyl cellulose (CMC) was added to immobilize the fluorescent labeled nanoparticles. 8% stock solution of CMC was prepared, the remaining constituent being deionized water. Formulation A consists of a diluted stock (50% stock and 50% deionized water) and acetone (3.3%). Formulation B consists of 22.5% polystyrene beads (highly concentrated by centrifuge) plus 77.5% acetone. A 1:1 mixture of formulation A and B was made. The following protocol was followed: (1) Dip a stent in formulation B (twice) then air dry; (2) Fluorescent image; (3) Dip the stent into formulation AB once; (4) Vacuum dry overnight; (5) Fluorescent image; (6) Saline dipping at 37 deg. C. for 10 minutes; (7) Vacuum dry for ½ hour; (8) Fluorescent image; (9) Saline dipping the stent again at 37 deg. C. for 20 minutes; (10) Vacuum dry for ½ hour; and (11) Fluorescent image.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of modifying a stent with nano-constructs, comprising:
   (a) applying a retaining fluid to the stent;
   (b) immersing the stent being wet from the retaining fluid into a second fluid having a suspension of nano-constructs, the nano-constructs comprising a polymeric component; and
   (c) removing the stent from the second fluid and allowing the retaining fluid and the second fluid to be removed such that the nano-constructs are carried by the stent for in vivo application of the constructs to a target location of a mammalian subject;
   wherein the retaining fluid is a non-solvent for the polymeric component of the nano-constructs.

2. The method of claim 1, wherein the stent comprises a polymeric component such that the nano-constructs attach to the surface of the polymeric component of the stent or become embedded within the polymeric component of the stent;
wherein the polymeric component of the stent may be the same as or different from the polymeric component of the nano-constructs.

3. The method of claim 2, wherein the retaining fluid is a non-solvent for the polymeric component of the stent.

4. The method of claim 2, wherein the polymeric component of the stent is a coating on a surface of the stent.

5. The method of claim 2, wherein a strut structure of the stent is made at least in part from the polymeric component of the stent.

6. The method of claim 2, wherein the polymeric component of the stent is biodegradable and is (i) at least part of a coating on a surface of the stent; (ii) a strut of the stent is made from the polymeric component; or (iii) a combination of (i) and (ii).

7. The method of claim 2, wherein
the retaining fluid is a solvent for the polymeric component of the stent, such that the duration of exposure of the retaining fluid to the polymeric component of the stent is limited until
(a) a tacky region is formed on the outermost surface of the polymeric component of the stent; or
(b) the retaining fluid causes the polymeric component of the stent to swell.

8. The method of claim 1, wherein the nano-constructs become embedded into (i) pores or cracks in a surface of the stent or (ii) pores or cracks in a surface of a coating deposited on the stent.

9. The method of claim 1, wherein the stent comprises a polymeric component comprising a bioactive agent.

10. The method of claim 7, wherein the duration of exposure of the retaining fluid to the polymeric component of the stent is limited until a tacky region is formed on the outermost surface of the polymeric component of the stent.

11. The method of claim 7, wherein the duration of exposure of the retaining fluid to the polymeric component is limited until the retaining fluid causes the polymeric component of the stent to swell.

12. The method of claim 6, wherein the polymeric component forming the strut structure is poly(lactic acid-co-glycolic acid), polylactic acid, polycaprolactone, or any combination thereof.

13. The method of claim 1, wherein the nano-constructs comprise a bioactive agent.

14. The method of claim 13, wherein the polymeric component of the nano-constructs comprises a polymeric nanoshell around a core comprising the bioactive agent.

15. The method of claim 13, wherein the nano-constructs comprise a metallic nanoshell with a core of a blend of the bioactive agent and the polymer of the polymeric component.

16. The method of claim 13, wherein the bioactive agent is coated on the surface of the nano-constructs.

17. The method of claim 1, further comprising after the removal of the retaining fluid and the second fluid, applying a topcoat to the stent, the topcoat comprising hyaluronic acid, polyhydroxypropyl methacrylamide (PHPMA), polycarboxymethyl cellulose (PCMC), gelatin, silk-elastin, elastin-collagen blend, polyacrylic acid, or any combination thereof.

18. The method of claim 13, wherein the bioactive agent of the nano-constructs is blended with a metallic material, a ceramic material, or any combination thereof, and optionally, the polymer of the polymeric component of the nano-constructs.

19. The method of claim 1, wherein the nano-constructs are of average size from 1 nm to 900 nm.

20. The method of claim 13, wherein the bioactive agent of the nano-constructs is blended with the polymer of the polymeric component of the nano-constructs, and optionally other materials.

\* \* \* \* \*

UNITED STATES PATENT AND TRADEMARK OFFICE
CERTIFICATE OF CORRECTION

| | | |
|---|---|---|
| PATENT NO. | : 8,802,184 B2 | Page 1 of 1 |
| APPLICATION NO. | : 11/809045 | |
| DATED | : August 12, 2014 | |
| INVENTOR(S) | : Hossainy et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1088 days.

Signed and Sealed this
Ninth Day of August, 2016

Michelle K. Lee
*Director of the United States Patent and Trademark Office*